(12) United States Patent
Worrell et al.

(10) Patent No.: US 11,877,789 B2
(45) Date of Patent: *Jan. 23, 2024

(54) DUAL AXLE ROBOTIC END EFFECTOR

(71) Applicant: CILAG GMBH INTERNATIONAL, Zug (CH)

(72) Inventors: Barry Christian Worrell, Maineville, OH (US); Joseph Michael Mueller, South Lebanon, OH (US); Rudolph Henry Nobis, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,592

(22) Filed: May 2, 2022

(65) Prior Publication Data

US 2022/0257308 A1  Aug. 18, 2022

Related U.S. Application Data

(63) Continuation of application No. 15/971,258, filed on May 4, 2018, now Pat. No. 11,317,962.

(51) Int. Cl.

| A61B 18/14 | (2006.01) |
| A61B 34/30 | (2016.01) |
| A61B 17/29 | (2006.01) |
| A61B 34/37 | (2016.01) |
| A61B 34/00 | (2016.01) |

(Continued)

(52) U.S. Cl.
CPC .......... *A61B 18/1442* (2013.01); *A61B 34/37* (2016.02); *A61B 34/71* (2016.02); *A61B 90/361* (2016.02); *A61B 2017/00477* (2013.01); *A61B 2017/00853* (2013.01); *A61B 2017/2926* (2013.01); *A61B 2017/2939* (2013.01); *A61B 2034/305* (2016.02)

(58) Field of Classification Search
CPC ...... A61B 2017/2939; A61B 2034/305; A61B 18/1442; A61B 34/37; A61B 34/71; A61B 17/00234; A61B 2017/00477; A61B 2034/302; A61B 34/70
See application file for complete search history.

(56) References Cited

U.S. PATENT DOCUMENTS 4,669,471 A * 6/1987 Hayashi ......... A61B 17/320016
228/139
5,257,558 A * 11/1993 Farzin-Nia ............... A61C 7/04
81/418

(Continued)

FOREIGN PATENT DOCUMENTS

| JP | 2016112063 A | 6/2016 |
| WO | 2016025132 A1 | 2/2016 |

*Primary Examiner* — Sean W Collins

(57) ABSTRACT

An end effector includes a distal clevis, an axle mounted to the distal clevis, a first jaw holder and corresponding first jaw member rotatably mounted to the axle, and second jaw holder and corresponding second jaw member rotatably mounted to the axle. A cylindrical sleeve axle having opposing first and second ends and defining a central passageway extending between the opposing first and second ends, the sleeve axle providing a continuously straight and uninterrupted outer surface extending entirely between the opposing first and second ends. The axle is received within the central passageway and the sleeve axle is rotatable relative to the axle.

20 Claims, 5 Drawing Sheets

(51) Int. Cl.
  *A61B 90/00* (2016.01)
  *A61B 17/00* (2006.01)

(56) References Cited

U.S. PATENT DOCUMENTS

| | | | |
|---|---|---|---|
| 6,394,998 B1* | 5/2002 | Wallace | A61B 34/35 |
| | | | 901/29 |
| 7,824,401 B2 | 11/2010 | Manzo et al. | |
| 9,204,923 B2 | 12/2015 | Manzo et al. | |
| 11,317,962 B2* | 5/2022 | Worrell | A61B 34/37 |
| 2004/0073208 A1* | 4/2004 | Sutter | A61B 17/2816 |
| | | | 606/49 |
| 2013/0018373 A1* | 1/2013 | Lau | A61B 18/085 |
| | | | 606/48 |
| 2015/0025571 A1 | 1/2015 | Suzuki | |
| 2017/0224367 A1 | 8/2017 | Kapadia | |
| 2017/0265925 A1* | 9/2017 | Garrison | A61B 18/085 |
| 2018/0193086 A1* | 7/2018 | Robert | B25J 15/0226 |

\* cited by examiner

DUAL AXLE ROBOTIC END EFFECTOR

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. Although not necessary, the instrument's end effector can be articulated (moved) using a cable driven motion system having one or more drive cables that extend through the wrist joint. A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

To ensure accurate and responsive end effector articulation, the drive cables are maintained at elevated tensile loads. At such elevated tensile loads, the axle that governs articulation of the end effector in yaw motion can begin to gall, which can generate excess friction and contribute to cable breakage. Galling of the axles is exacerbated in end effectors having opposing jaws or blades with jaw holders that rotate independently against the axle. Galling between the axle and the jaw holders increases friction, which reduces cable life.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to surgical instruments having an end effector that incorporates a dual axle construction where one axle resides inside a hollow outer axle to increase the bearing surface and reduce galling.

Embodiments discussed herein describe surgical instruments that incorporate cable-driven end effectors with an improved axle that helps mitigate galling. One example end effector includes a distal clevis, an axle mounted to the distal clevis, a first jaw holder and corresponding first jaw member rotatably mounted to the axle, and a second jaw holder and corresponding second jaw member rotatably mounted to the axle. A sleeve axle radially interposes the axle and the jaw holders. The sleeve axle has a first end, a second end, and a central passageway extending between the first and second ends. The axle may be received within the central passageway and the sleeve axle is rotatable relative to the axle. Various portions of the axle and the sleeve axle may also be coated or otherwise include a wear-resistant substance to mitigate wear and friction.

Figure 1:
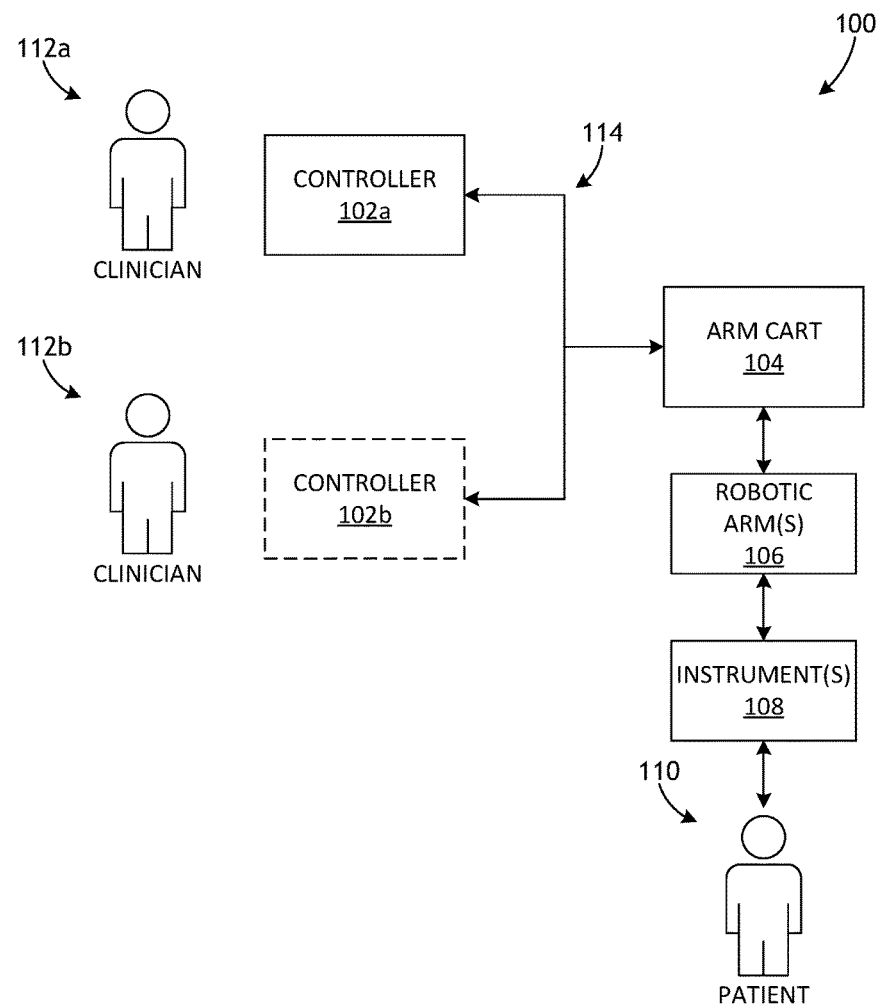
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104, although the arm cart 104 is not necessarily required. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s)

108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
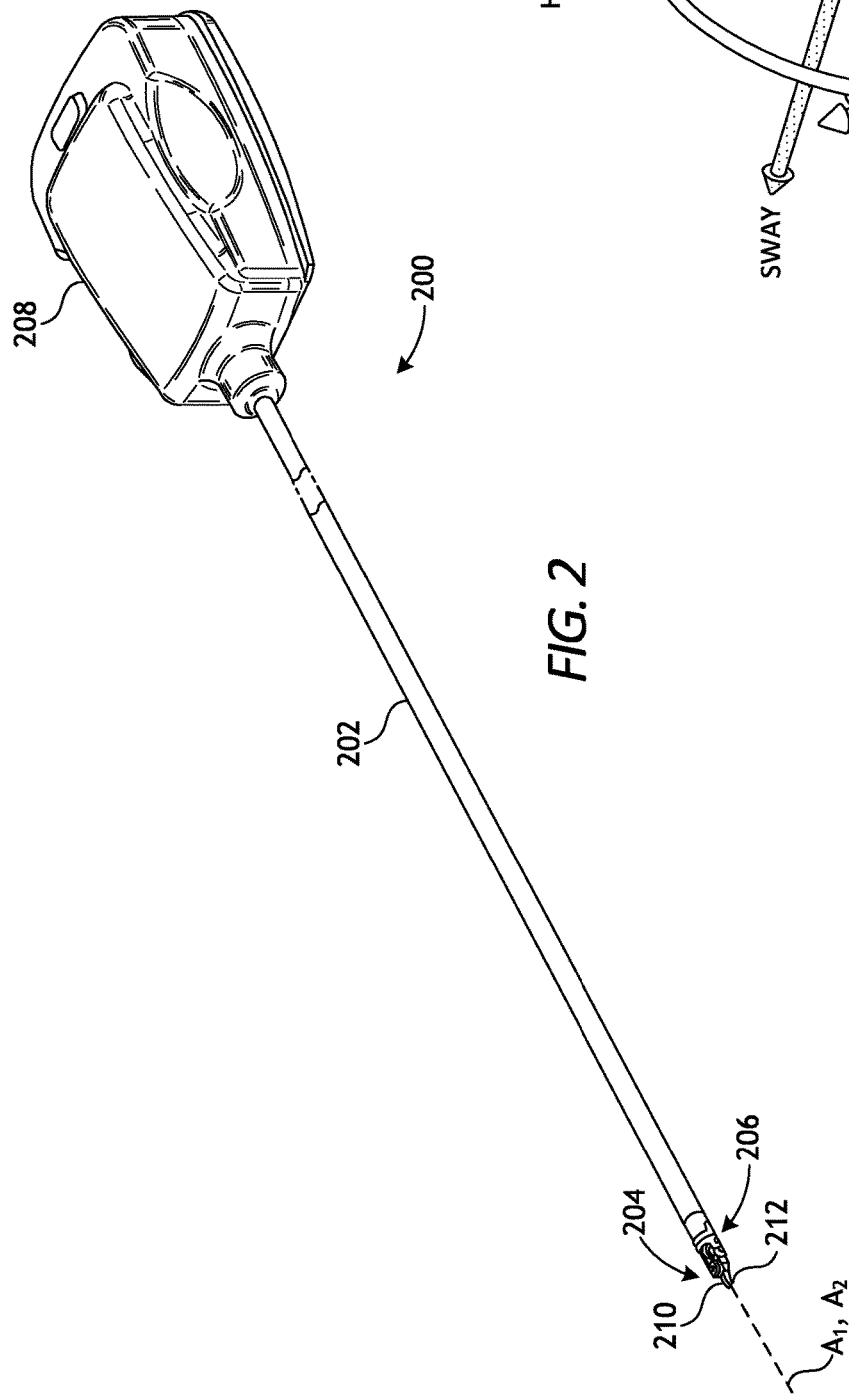
FIG. 2 is a side view of an example surgical tool that may incorporate some or all of the principles of the present disclosure.

FIG. 2 is side view of an example surgical tool 200 that may incorporate some or all of the principles of the present disclosure. The surgical tool 200 may be the same as or similar to the surgical instrument(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. The housing 208 includes (contains) various mechanisms designed to control operation of various features associated with the end effector 204 (e.g., clamping, firing, rotation, articulation, energy delivery, etc.). In at least some embodiments, the shaft 202, and hence the end effector 204 coupled thereto, is configured to rotate about a longitudinal axis $A_1$ of the shaft 202. In such embodiments, at least one of the mechanisms included (housed) in the housing 208 is configured to control rotational movement of the shaft 202 about the longitudinal axis $A_1$.

The surgical tool 200 can have any of a variety of configurations capable of performing at least one surgical function. For example, the surgical tool 200 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can have a variety of sizes, shapes, and configurations. In the illustrated embodiment, the end effector 204 comprises surgical scissors that include opposing jaws 210, 212 (alternately referred to as "blades") configured to move (articulate) between open and closed positions. As will be appreciated, however, the opposing jaws 210, 212 may alternatively form part of other types of end effectors such as, but not limited to, a tissue grasper, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot at the wrist 206 to articulate the end effector 204 between the open and closed positions.

Figure 3:
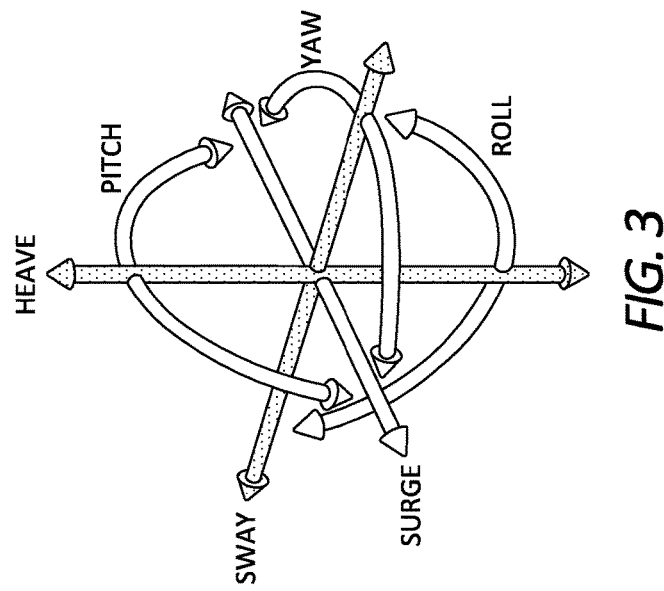
FIG. 3 illustrates potential degrees of freedom in which the wrist of FIG. 1 may be able to articulate (pivot).

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 204) with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) at least some of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Figure 4:
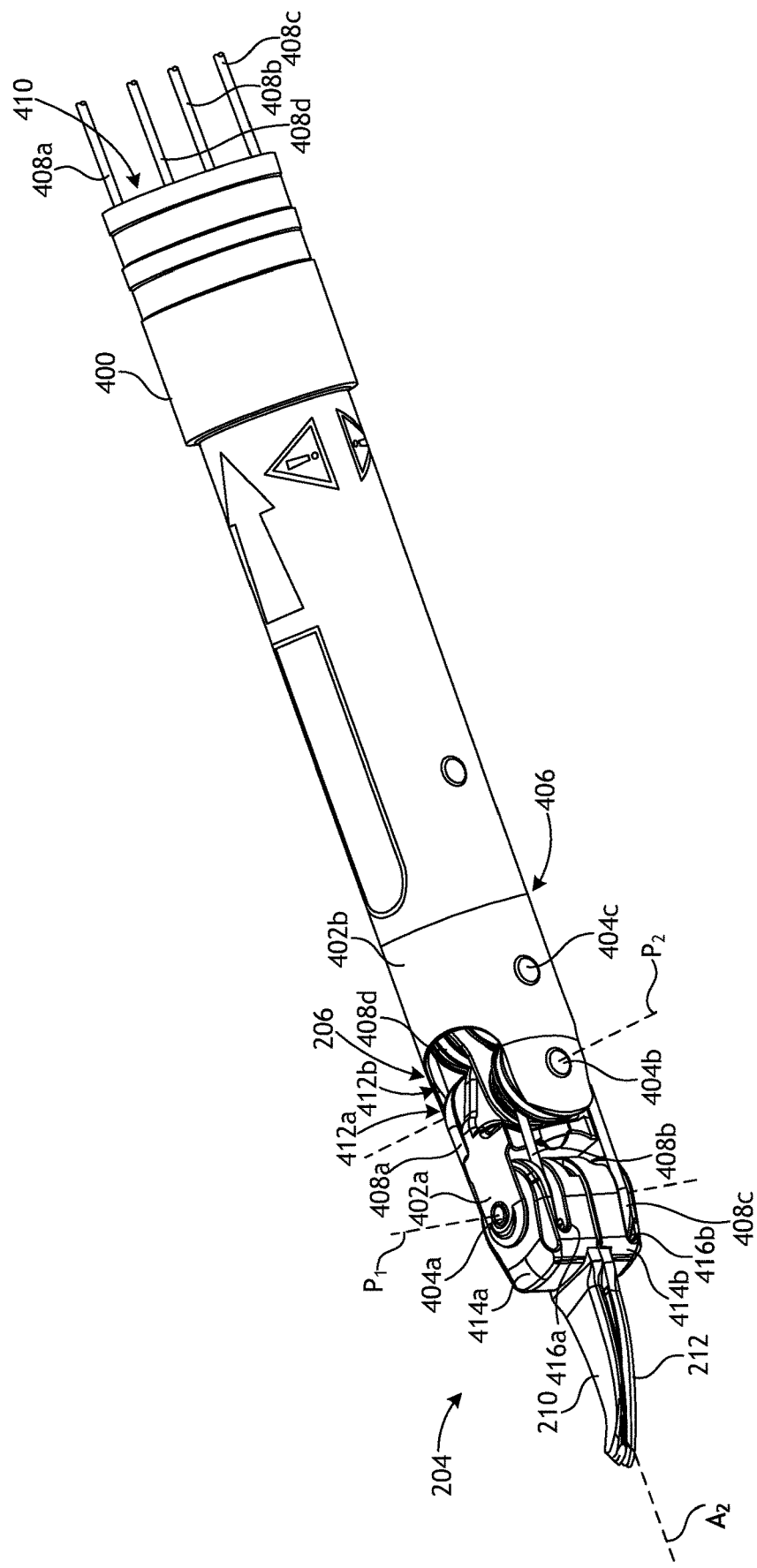
FIG. 4 is an enlarged isometric view of the distal end of the surgical tool of FIG. 1.

FIG. 4 is an enlarged isometric view of the distal end of the surgical tool 200 of FIG. 2. More specifically, FIG. 4 depicts enlarged views of the end effector 204 and the wrist 206, with the end effector 204 in the unarticulated position. The wrist 206 operatively couples the end effector 204 to the shaft 202 (FIG. 2). In the illustrated embodiment, however, a shaft adapter 400 may be directly coupled to the wrist 206 and otherwise interpose the shaft 202 and the wrist 206. In other embodiments, the shaft adapter 400 may be omitted and the shaft 202 may instead be directly coupled to the wrist 206, without departing from the scope of the disclosure. As used herein, the term "operatively couple" refers to a direct or indirect coupling engagement. Accordingly, the wrist 206 may be operatively coupled to the shaft 202 either through a direct coupling engagement where the wrist 206 is directly coupled to the distal end of the shaft 202, or an indirect coupling engagement where the shaft adapter 400 interposes the wrist 206 and the distal end of the shaft 202.

To operatively couple the end effector 204 to the shaft 202 (e.g., via the shaft adapter 400), the wrist 206 includes a distal clevis 402a and a proximal clevis 402b. The end effector 204 (i.e., the jaws 210, 212) is rotatably mounted to the distal clevis 402a at a first axle 404a, the distal clevis 402a is rotatably mounted to the proximal clevis 402b at a second axle 404b, and the proximal clevis 402b is coupled to a distal end 406 of the shaft adapter 400 (or alternatively the distal end of the shaft 202 of FIG. 2).

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. In the illustrated embodiment, the jaws 210, 212 are mounted at the first pivot axis $P_1$ thereby allowing the jaws 210, 212 to pivot relative to each other to open and close the end effector 204 or alternatively pivot in tandem to articulate the orientation of the end effector 204.

A plurality of drive cables, shown as drive cables 408a, 408b, 408c, and 408d, extend longitudinally within a lumen 410 defined by the shaft adapter 400 (and/or the shaft 202 of FIG. 2) and pass through the wrist 206 to be operatively coupled to the end effector 204. While four drive cables 408a-d are depicted in FIG. 4, more or less than four drive cables 408a-d may be included, without departing from the scope of the disclosure.

The drive cables 408a-d form part of the cable driven motion system briefly described above, and may be referred to and otherwise characterized as cables, bands, lines, cords, wires, ropes, strings, twisted strings, elongate members, etc. The drive cables 408a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 410 can be a single lumen, as illustrated, or can alternatively comprise a plurality of independent lumens that each receive one or more of the drive cables 408a-d.

The drive cables 408a-d extend proximally from the end effector 204 to the drive housing 208 (FIG. 2) where they are operatively coupled to various actuation mechanisms or devices housed (contained) therein to facilitate longitudinal movement (translation) of the drive cables 408a-d within the lumen 410. Selective actuation of all or a portion of the drive cables 408a-d causes the end effector 204 (e.g., one or both of the jaws 210, 212) to articulate (pivot) relative to the shaft 202. More specifically, selective actuation causes a corresponding drive cable 408a-d to translate longitudinally within the lumen 410 and thereby cause pivoting movement of the end effector 204. One or more drive cables 408a-d, for example, may translate longitudinally to cause the end effector 204 to articulate (e.g., both of the jaws 210, 212 angled in a same direction), to cause the end effector 204 to open (e.g., one or both of the jaws 210, 212 pivot away from the other), or to cause the end effector 204 to close (e.g., one or both of the jaws 210, 212 pivot toward the other).

Moving the drive cables 408a-d can be accomplished in a variety of ways, such as by triggering an associated actuator or mechanism operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202.

The wrist 206 includes a first plurality of pulleys 412a and a second plurality of pulleys 412b, each configured to interact with and redirect the drive cables 408a-d for engagement with the end effector 204. The first plurality of pulleys 412a is mounted to the proximal clevis 402b at the second axle 404b and the second plurality of pulleys 412b is also mounted to the proximal clevis 402b but at a third axle 404c located proximal to the second axle 404b. The first and second pluralities of pulleys 412a,b cooperatively redirect the drive cables 408a-d through an "S" shaped pathway before the drive cables 408a-d are operatively coupled to the end effector 204.

In at least one embodiment, one pair of drive cables 408a-d is operatively coupled to each jaw 210, 212 and configured to "antagonistically" operate the corresponding jaw 210, 212. In the illustrated embodiment, for example, the first and second drive cables 408a,b are coupled with a connector (not shown) at the first jaw 210, and the third and fourth drive cables 408c,d are coupled with a connector (not shown) at the second jaw 212. Consequently, actuation of the first drive cable 408a pivots the first jaw 210 about the first pivot axis $P_1$ toward the open position, and actuation of the second drive cable 408b pivots the first jaw 210 about the first pivot axis $P_1$ in the opposite direction and toward the closed position. Similarly, actuation of the third drive cable 408c pivots the second jaw 212 about the first pivot axis $P_1$ toward the open position, while actuation of the fourth drive cable 408d pivots the second jaw 212 about the first pivot axis $P_1$ in the opposite direction and toward the closed position.

Accordingly, the drive cables 408a-d may be characterized or otherwise referred to as "antagonistic" cables that cooperatively (yet antagonistically) operate to cause relative or tandem movement of the first and second jaws 210, 212. When the first drive cable 408a is actuated (moved), the second drive cable 408b naturally follows as coupled to the first drive cable 408a, and when the third drive cable 408c is actuated, the fourth drive cable 408d naturally follows as coupled to the third drive cable 408c, and vice versa.

The end effector 204 further includes a first jaw holder 414a and a second jaw holder 414b laterally offset from the first jaw holder 414a. The first jaw holder 414a is mounted to the first axle 404a and configured to receive and seat the first jaw 210 such that movement (rotation) of the first jaw holder 414a about the first pivot axis $P_1$ correspondingly moves (rotates) the first jaw 210. The first jaw holder 414a may also provide and otherwise define a first pulley 416a configured to receive and seat one or more drive cables, such as the first and second drive cables 408a,b to effect such movement (rotation). The second jaw holder 414b is similarly mounted to the first axle 404a and is configured to receive and seat the second jaw 212 such that movement (rotation) of the second jaw holder 414b about the first pivot axis $P_1$ correspondingly moves (rotates) the second jaw 212. The second jaw holder 414b may also provide and otherwise define a second pulley 416b configured to receive and seat one or more drive cables, such as the third and fourth drive cables 408c,d, to effect such movement (rotation).

The term "jaw holder," as used herein, is intended to apply to a variety of types of end effectors having opposing jaws or blades that are rotatably pivotable (movable) relative to one another. In the illustrated embodiment, the jaws 210, 212 comprise opposing scissor blades of a surgical scissors end effector. Accordingly, the jaw holders 414a,b may alternately be referred to as "blade holders". In other embodiments, however, the jaws 210, 212 may alternatively comprise opposing jaws used in a grasper end effector, or the like, and the term "jaw holder" similarly applies, without departing from the scope of the disclosure. Moreover, the term "holder" in "jaw holder" may be replaced with "mount," "drive member," or "actuation member."

Figure 5:
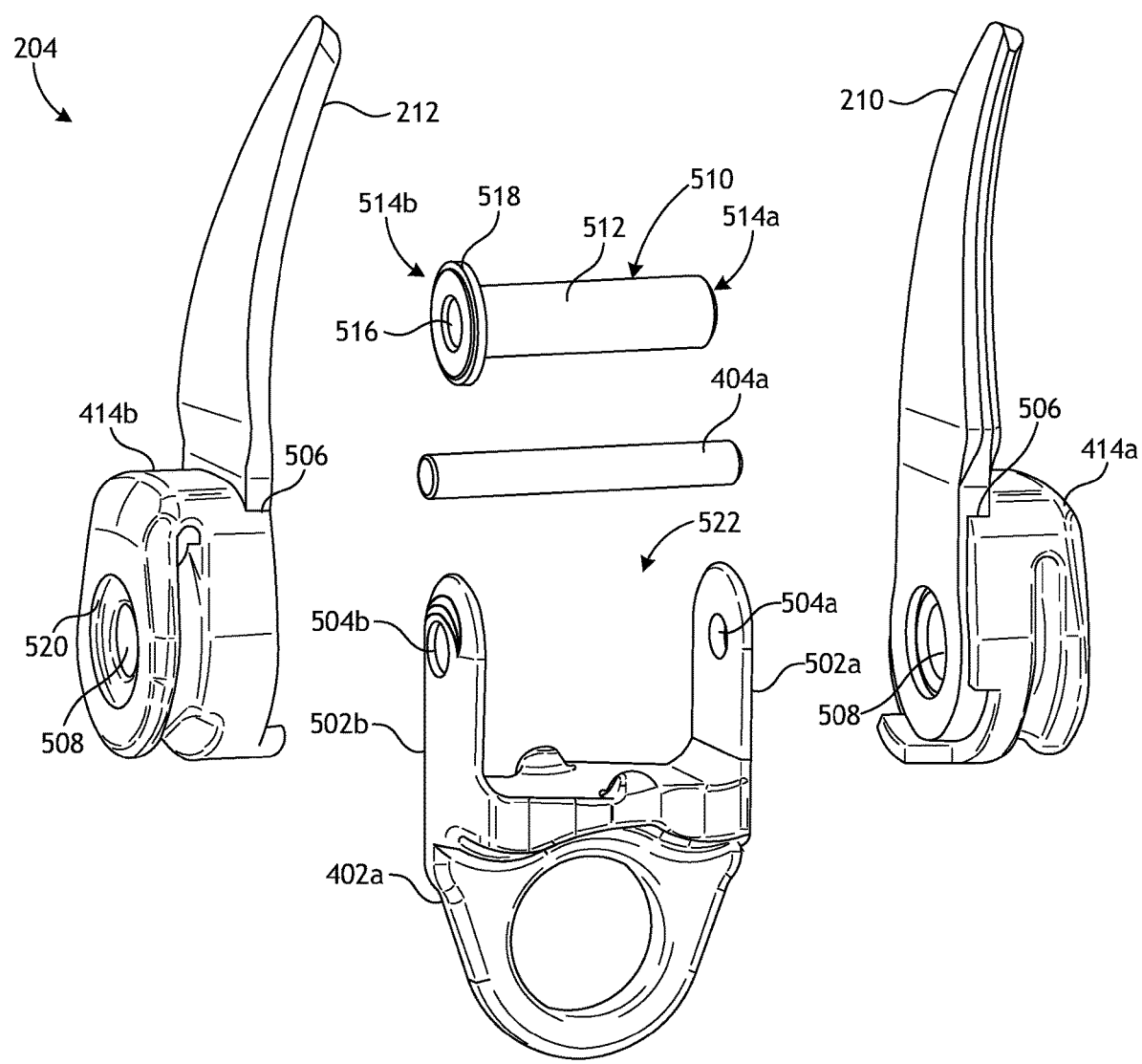
FIG. 5 is an exploded view of a portion of the end effector of FIG. 4.

FIG. 5 is an exploded view of a portion of the end effector 204, according to one or more embodiments of the disclosure. More specifically, FIG. 5 depicts the distal clevis 402a, the first and second jaw members 210, 212 mounted to their respective first and second jaw holders 414a,b, and the first axle 404a.

As illustrated, the distal clevis 402a includes a first distally-extending arm 502a and a second distally-extending arm 502b offset from the first distally-extending arm 502a. The first arm 502a defines a first aperture 504a configured to receive and seat one end of the first axle 404a, and the second arm 502b defines a second aperture 504b configured to receive and seat the opposite end of the first axle 404a.

The first and second jaw members 210, 212 may be mounted to the first and second jaw holders 414a,b, respectively, such that movement of the particular jaw holder 414a,b will correspondingly move the mounted jaw member 210, 212. In the illustrated embodiment, for example, the first and second jaw holders 414a,b may each provide or otherwise define a jaw recess 506 sized to receive and seat the jaw members 210, 212. The jaw holders 414a,b may also each define a central aperture 508 through which the first axle 404a may extend to rotatably mount the jaw members 210, 212 to the distal clevis 402a.

In the illustrated embodiment, the end effector 204 may further include a sleeve axle 510 that may be designed to assume some or all of the bearing stress caused by independent rotation of the jaw holders 414a,b during operation. As illustrated, the sleeve axle 510 comprises a generally hollow and cylindrical body 512 having a first end 514a and a second end 514b opposite the first end 514a. A central passageway 516 is defined in the body 512 and extends between the first and second ends 514a,b. The central passageway 516 may be sized or otherwise configured to receive the first axle 404a therein. When the end effector 204 is fully assembled, the sleeve axle 510 interposes the first axle 404a and the jaw holders 414a,b. Accordingly, the sleeve axle 510 may mitigate or entirely eliminate galling on the first axle 404a, which could otherwise limit the useful service life of the end effector 204.

In some embodiments, as illustrated, the sleeve axle 510 may provide or otherwise define an enlarged-diameter head 518 at the second end 514b to help properly position the sleeve axle 510 for operation. More specifically, the sleeve axle 510 may be extendable through the coaxially aligned central apertures 508 of each jaw holder 414a,b, and the enlarged-diameter head 518 may be sized to be received into an end recess 520 defined on the second jaw holder 414b. In at least one embodiment, the depth of the end recess 520 may allow the enlarged-diameter head 518 to be received in a flush-mount arrangement with the remaining portions of the second jaw holder 414a, but may alternatively protrude a short distance to act as a bearing against an inner surface of the distal clevis 402a.

To assemble the end effector 204, the sleeve axle 510 is extended through the coaxially aligned central apertures 508 of each jaw holder 414a,b until the enlarged-diameter head 518 is received within the end recess 520. In some embodiments, the sleeve axle 510 may be coupled to the first jaw holder 414a to secure the sleeve axle 510 in place. In conjunction with the enlarged-diameter head 518 being received within the end recess 520, securing the sleeve axle 510 to the first jaw holder 414a may essentially couple the first jaw holder 414a to the second jaw holder 414b.

The first and second jaw holders 414a,b may then be positioned in an opening 522 defined between the opposing arms 502a,b of the distal clevis 402a. The first axle 404a may then be progressively extended through the first aperture 504a in the first arm 502a, the central passageway 516 of the sleeve axle 510, and the second aperture 504b in the second arm 502b. One or both ends of the first axle 404a may then be secured to the distal clevis 402a at the first or second apertures 504a,b to secure the first axle 404a to the distal clevis 402a.

Figure 6:
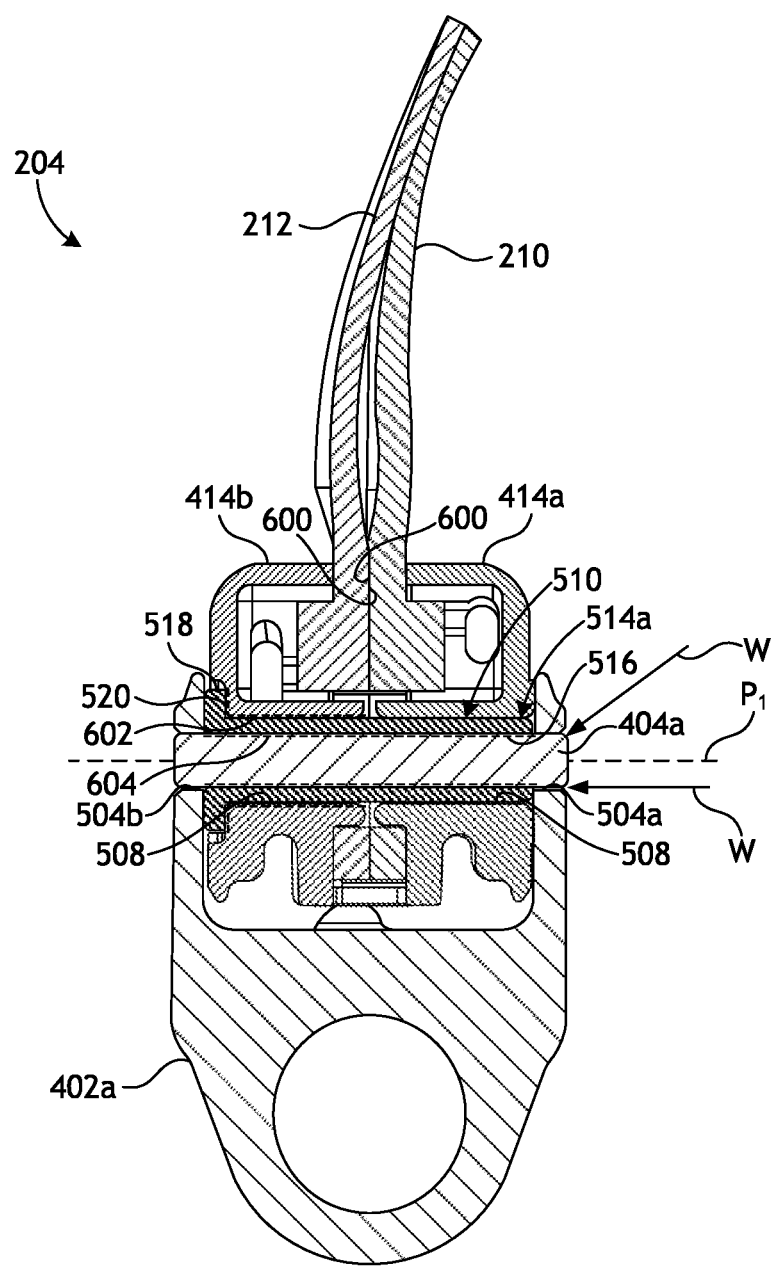
FIG. 6 is a cross-sectional side view of the end effector of FIG. 5 as assembled.

FIG. 6 is a cross-sectional side view of the end effector 204 of FIG. 5 as assembled, according to one or more embodiments. As illustrated, the sleeve axle 510 generally interposes the first axle 404a and the first and second jaw holders 414a,b. More specifically, the sleeve axle 510 is extended through the coaxially aligned central apertures 508 of the jaw holders 414a,b and the enlarged-diameter head 518 is received into the end recess 520 of the second jaw holder 414b. Moreover, the first axle 404a extends through the central passageway 516 of the sleeve axle 510.

The sleeve axle 510 may be secured to the first jaw holder 414a via a variety of means. In some embodiments, for example, the sleeve axle 510 may be welded or brazed to the first jaw holder 414a at the first end 514a, as shown by the arrows W. In other embodiments, however, the sleeve axle 510 may be threaded to the first jaw holder 414a via a mating threaded engagement, without departing from the scope of the disclosure.

In some embodiments, a compressive load (force) may be applied to the first jaw holder 414a along the sleeve axle 510 as the sleeve axle 510 is secured to the first jaw holder 414a. The compressive load may force the enlarged-diameter head 518 against the second jaw holder 414b at the end recess 520, and thereby remove any gaps between the jaw holders 414a,b to provide a zero tolerance stack. This may prove advantageous in trapping the jaw members 210, 212 within the assembly such that the jaw members 210, 212 need not be welded to the respective jaw holders 414a,b. Moreover, securing the sleeve axle 510 to the first jaw holder 414a while a compressive load (force) is applied ensures that opposing axial bearing surfaces 600 of the jaw members 210, 212 are maintained parallel to one another during operation. This may prove advantageous in assuring face-to-face contact at the midline between of the jaw members 210, 212 while opening and closing the jaw members 210, 212.

Since the sleeve axle 510 is secured to the first jaw holder 414a, movement (articulation) of the first jaw holder 414a correspondingly rotates the sleeve axle 510 about the first pivot axis $P_1$ In contrast, the second jaw holder 414b may be free to move (articulate) relative to the sleeve axle 510 during operation. Consequently, as the scissoring action of the jaw members 210, 212 takes place, the sleeve axle 510 assumes the bearing stress at the interface between the sleeve axle 510 and the second jaw holder 414b.

In some embodiments, the end effector 204 may include a wear-resistant substance 602 (shown as dashed lines) provided at the radial interface between the sleeve axle 510 and the second jaw holder 414b to reduce friction and wear. In one embodiment, the wear-resistant substance 602 may comprise a material coated on the outer radial surface of the sleeve axle 510, but could alternatively (or in addition thereto) comprise a material coated on the inner radial surface of the second jaw holder 414b at the central aperture 508. In yet other embodiments, the wear-resistant substance 602 may comprise a low-friction bearing material or structure that interposes the sleeve axle 510 and the second jaw holder 414b. The wear-resistant substance 602 may comprise a low-friction material such as, but not limited to, a diamond-like carbon (DLC), an ultra-hard material (e.g., polycrystalline diamond, polycrystalline cubic boron nitride, or impregnated diamond), a lubricant (e.g., KRYTOX™ brand synthetic lubricant), a dry film coating (e.g., TEFLON®, graphite, etc.), or any combination thereof. Alternatively, the second jaw holder 414b may be machined out of a spinodal bronze or another material that offers good galling resistance and strength against stainless steel, for example.

In some embodiments, the wear-resistant substance 602 may also be provided at the axial interface between the sleeve axle 510 and the second jaw holder 414b. More particularly, the wear-resistant substance 602 may extend to the axial interface between the enlarged-diameter head 518 and the end recess 520 to reduce friction and wear at that location as the sleeve axle 510 rotates relative to the second jaw holder 414b, and vice versa.

The first axle 404a supports the jaw holders 414a,b and the sleeve axle 510 on the distal clevis 402a and thereby controls the yaw motion of the end effector 204 when the jaw members 210, 212 move in unison. More specifically, the first axle 404a extends through the central passageway 516 of the sleeve axle 510 and its opposing ends are received within the first and second apertures 504a,b, respectively, of the distal clevis 402a. In some embodiments, one or both ends of the first axle 404a may be secured to the distal clevis 402a at the first or second apertures 504a,b, respectively.

To secure the first axle 404a to the distal clevis 402a, one or both ends of the first axle 404a may be welded or brazed to the distal clevis 402a at the first or second apertures 504a,b. In other embodiments, one end of the first axle 404a may be threaded to the corresponding aperture 504a,b. In yet other embodiments, one or both of the ends of the first axle 404a may be secured to the corresponding apertures 504a,b by orbital riveting the outer surface of the ends of the first axle 404a. In even further embodiments, one or both ends of the first axle 404a may be received within the corresponding aperture 504a,b via an interference or shrink fit.

Since the first axle 404a is secured to the distal clevis 402a, the jaw holders 414a,b and the sleeve axle 510 may each be able to move (articulate) relative to the first axle 404a about the first pivot axis $P_1$ Having the sleeve axle 510 interpose the first axle 404a and the jaw holders 414a,b effectively spreads the bearing contact over the entire axial length of the first axle 404a via movement of the sleeve axle 510.

In some embodiments, a wear-resistant substance 604 (shown as dashed lines) may be provided at the interface between the first axle 404a and the sleeve axle 510 to reduce friction and wear. The wear-resistant substance 604 may comprise similar materials or structures as the wear-resistant substance 602 mentioned above. The wear-resistant substance 604 may comprise a material coated on the outer radial surface of the first axle 404a, or alternatively (or in addition thereto) on the inner radial surface of the sleeve axle 510. In other embodiments, the wear-resistant substance 604 may comprise a low-friction bearing material or structure interposing the first axle 404a and the sleeve axle 510.

Embodiments disclosed herein include:

A. An end effector that includes a distal clevis, an axle mounted to the distal clevis, a first jaw holder and corresponding first jaw member rotatably mounted to the axle, a second jaw holder and corresponding second jaw member rotatably mounted to the axle, and a sleeve axle having a first end, a second end, and a central passageway extending between the first and second ends, wherein the axle is received within the central passageway and the sleeve axle is rotatable relative to the axle.

B. A surgical tool that includes a drive housing, an elongate shaft that extends from the drive housing, a wrist operatively coupled to a distal end of the shaft and having a distal clevis and an axle mounted to the distal clevis, an end effector having a first jaw holder and corresponding first jaw member rotatably mounted to the axle and a second jaw holder and corresponding second jaw member rotatably mounted to the axle, and a sleeve axle radially interposing the first and second jaw holders and the axle and rotatable relative to the axle.

C. A method of operating a surgical tool that includes positioning the surgical tool adjacent a patient for operation, the surgical tool including a drive housing, an elongate shaft that extends from the drive housing, a wrist operatively coupled to a distal end of the shaft and having a distal clevis and an axle mounted to the distal clevis, an end effector having a first jaw holder and corresponding first jaw member rotatably mounted to the axle and a second jaw holder and corresponding second jaw member rotatably mounted to the axle, and a sleeve axle radially interposing the first and second jaw holders and the axle and rotatable relative to the axle. The method further including articulating at least one of the first and second jaw members about the axle, and mitigating galling of the axle with the sleeve axle.

Each of embodiments A, B, and C may have one or more of the following additional elements in any combination: Element 1: wherein the sleeve axle is secured to the first jaw holder such that movement of the first jaw holder causes the sleeve axle to rotate. Element 2: wherein the first end of the sleeve axle is welded or brazed to the first jaw holder. Element 3: further comprising a wear-resistant substance provided at a radial interface between the sleeve axle and the second jaw holder. Element 4: wherein the wear-resistant substance comprises a material coated on one or both of an outer radial surface of the sleeve axle and an inner radial surface of the second jaw holder. Element 5: further comprising an enlarged-diameter head provided at the second end and receivable within an end recess defined on the second jaw holder. Element 6: further comprising a wear-resistant substance provided at an axial interface between the enlarged-diameter head and the end recess. Element 7: further comprising a wear-resistant substance provided at an interface between the first axle and the sleeve axle. Element 8: wherein the wear-resistant substance comprises a material coated on one or both of an outer radial surface of the first axle and an inner radial surface of the sleeve axle. Element 9: wherein opposing ends of the first axle are received within corresponding apertures defined in the distal clevis, and wherein one or both of the opposing ends are secured to the distal clevis at the corresponding apertures. Element 10: wherein the one or both of the opposing ends are secured to the distal clevis by at least one of welding, brazing, a threaded engagement, orbital riveting an interference fit, and a shrink fit.

Element 11: wherein the sleeve axle comprises a cylindrical body having a first end, a second end, and a central passageway extending between the first and second ends, and wherein the axle extends through the central passageway. Element 12: wherein the sleeve axle is secured to the first jaw holder such that movement of the first jaw holder causes the sleeve axle to rotate. Element 13: further comprising an enlarged-diameter head provided at the second end and receivable within an end recess defined on the second jaw holder. Element 14: further comprising a wear-resistant substance provided at an axial interface between the enlarged-diameter head and the end recess, wherein the wear-resistant substance comprises a low-friction material selected from the group consisting of a diamond-like carbon coating, an ultra-hard material, a lubricant, a dry film coating, and any combination thereof. Element 15: further comprising a wear-resistant substance provided at a radial interface between the sleeve axle and the second jaw holder, wherein the wear-resistant substance comprises a low-friction material selected from the group consisting of a diamond-like carbon coating, an ultra-hard material, a lubricant, a dry film coating, and any combination thereof. Element 16: further comprising a wear-resistant substance provided at an interface between the first axle and the sleeve axle, wherein the wear-resistant substance comprises a low-friction material selected from the group consisting of a diamond-like carbon coating, an ultra-hard material, a lubricant, a dry film coating, and any combination thereof. Element 17: wherein the second jaw holder is made of a material having a low galling threshold against stainless steel.

By way of non-limiting example, exemplary combinations applicable to A, B, and C include: Element 1 with Element 2; Element 3 with Element 4; Element 5 with Element 6; Element 7 with Element 8; Element 9 with Element 10; Element 11 with Element 12; Element 11 with Element 13; and Element 13 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:
1. An end effector, comprising:
   a distal clevis;
   an axle mounted to the distal clevis;
   a first jaw holder and corresponding first jaw member rotatably mounted to the axle;
   a second jaw holder and corresponding second jaw member rotatably mounted to the axle; and a cylindrical sleeve axle having opposing first and second ends and defining a central passageway extending between the opposing first and second ends, the sleeve axle providing a continuously straight and uninterrupted outer surface extending entirely between the opposing first and second ends, wherein the first end is housed within the first jaw holder and the second end is housed within the second jaw holder, wherein the axle is received within the central passageway and the sleeve axle is rotatable relative to the axle.

2. The end effector of claim 1, wherein the sleeve axle is secured to the first jaw holder such that movement of the first jaw holder causes the sleeve axle to rotate.

3. The end effector of claim 2, wherein the first end of the sleeve axle is welded or brazed to the first jaw holder.

4. The end effector of claim 1, further comprising a wear-resistant substance provided at a radial interface between the sleeve axle and the second jaw holder.

5. The end effector of claim 4, wherein the wear-resistant substance comprises a material coated on one or both of an outer radial surface of the sleeve axle and an inner radial surface of the second jaw holder.

6. The end effector of claim 1, wherein a head is provided at the second end of the sleeve axle and exhibits a diameter larger than a diameter of remaining portions of the sleeve axle, and wherein the head is received within an end recess defined on the second jaw holder.

7. The end effector of claim 6, further comprising a wear-resistant substance provided at an axial interface between the head and the end recess.

8. The end effector of claim 1, further comprising a wear-resistant substance provided at an interface between the axle and the sleeve axle.

9. The end effector of claim 8, wherein the wear-resistant substance comprises a material coated on one or both of an outer radial surface of the axle and an inner radial surface of the sleeve axle.

10. The end effector of claim 1, wherein opposing ends of the axle are received within corresponding apertures defined in the distal clevis, and wherein one or both of the opposing ends of the axle are secured to the distal clevis at the corresponding apertures and thereby prevent the axle from rotating relative to the distal clevis.

11. The end effector of claim 10, wherein the one or both of the opposing ends of the axle are secured to the distal clevis by at least one of welding, brazing, a threaded engagement, orbital riveting an interference fit, and a shrink fit.

12. The end effector of claim 1, wherein the first jaw holder provides a first pulley operable to receive and seat one or more first drive cables, and the second jaw holder provides a second pulley operable to receive and seat one or more second drive cables, and wherein actuation of the one or more first drive cables and the one or more second drive cables causes the corresponding first and second jaw members to pivot relative to one another.

13. A surgical tool, comprising:
a drive housing;
an elongate shaft that extends from the drive housing;
a wrist operatively coupled to a distal end of the shaft and having a distal clevis and an axle mounted to the distal clevis;
an end effector having a first jaw holder and corresponding first jaw member rotatably mounted to the axle and a second jaw holder and corresponding second jaw member rotatably mounted to the axle; and a cylindrical sleeve axle having opposing first and second ends and defining a central passageway extending between the opposing first and second ends, the sleeve axle providing a continuously straight and uninterrupted outer surface extending entirely between the opposing first and second ends, wherein the first end is housed within the first jaw holder and the second end is housed within the second jaw holder, wherein the sleeve axle radially interposes the first and second jaw holders and the axle and is rotatable relative to the axle.

14. The surgical tool of claim 13, wherein the axle extends through the central passageway.

15. The surgical tool of claim 13, wherein the sleeve axle is secured to the first jaw holder such that movement of the first jaw holder causes the sleeve axle to rotate.

16. The surgical tool of claim 13, wherein a head is provided at the second end of the sleeve axle and exhibits a diameter larger than a diameter of remaining portions of the sleeve axle, and wherein the head is received within an end recess defined on the second jaw holder.

17. The surgical tool of claim 16, further comprising a wear-resistant substance provided at an axial interface between the head and the end recess, wherein the wear-resistant substance comprises a low-friction material selected from the group consisting of a diamond-like carbon coating, an ultra-hard material, a lubricant, a dry film coating, and any combination thereof.

18. The surgical tool of claim 13, further comprising a wear-resistant substance provided at a radial interface between the sleeve axle and the second jaw holder, wherein the wear-resistant substance comprises a low-friction material selected from the group consisting of a diamond-like carbon coating, an ultra-hard material, a lubricant, a dry film coating, and any combination thereof.

19. The surgical tool of claim 13, further comprising a wear-resistant substance provided at an interface between the axle and the sleeve axle, wherein the wear-resistant substance comprises a low-friction material selected from the group consisting of a diamond-like carbon coating, an ultra-hard material, a lubricant, a dry film coating, and any combination thereof.

20. A method of operating a surgical tool, comprising:
positioning the surgical tool adjacent a patient for operation, the surgical tool including:
a drive housing;
an elongate shaft that extends from the drive housing;
a wrist operatively coupled to a distal end of the shaft and having a distal clevis and an axle mounted to the distal clevis;
an end effector having a first jaw holder and corresponding first jaw member rotatably mounted to the axle and a second jaw holder and corresponding second jaw member rotatably mounted to the axle; and
a cylindrical sleeve axle having opposing first and second ends and defining a central passageway extending between the opposing first and second ends, the sleeve axle providing a continuously straight and uninterrupted outer surface extending entirely between the opposing first and second ends, wherein the first end is housed within the first jaw holder and the second end is housed within the second jaw holder, and the axle is received within the central passageway such that the sleeve axle radially interposes the first and second jaw holders and the axle;
articulating at least one of the first and second jaw members about the axle, wherein the sleeve axle is rotatable relative to the axle; and
mitigating galling of the axle with the sleeve axle.

\* \* \* \* \*